(12) United States Patent
Xiang et al.

(10) Patent No.: US 6,924,150 B1
(45) Date of Patent: Aug. 2, 2005

(54) MAGNETIC RESONANCE IMAGING CONTRAST SYSTEM

(75) Inventors: Xiao Dong Xiang, Alameda, CA (US); Gerald F. Dionne, Winchester, MA (US); Haitao Yang, Albany, CA (US)

(73) Assignee: Intematix Corporation, Moraga, CA (US)

(*) Notice: Subject to any disclaimer, the term of this patent is extended or adjusted under 35 U.S.C. 154(b) by 190 days.

(21) Appl. No.: 10/124,203

(22) Filed: Apr. 17, 2002

Related U.S. Application Data (63) Continuation-in-part of application No. 10/071,563, filed on Feb. 9, 2002, now Pat. No. 6,693,426.

(51) Int. Cl.[7] .......................... A61B 5/055; A61B 8/00; G01N 25/18; G01R 33/00; G01V 3/00
(52) U.S. Cl. ..................... 436/173; 436/149; 324/300; 324/301; 324/307; 324/200; 424/9.3; 424/9.32; 424/9.323
(58) Field of Search ................. 436/149, 173, 436/806; 324/300, 301, 307, 200; 424/9.3, 9.32, 9.323

(56) References Cited

U.S. PATENT DOCUMENTS

| | | | | |
|---|---|---|---|---|
| 4,579,121 A | * | 4/1986 | Macovski | .................... 600/410 |
| 4,642,567 A | * | 2/1987 | Kaplan | ........................ 324/309 |
| 5,438,263 A | * | 8/1995 | Dworkin et al. | ............ 324/309 |
| 5,496,534 A | * | 3/1996 | Klaveness et al. | ......... 424/9.32 |
| 6,368,574 B1 | * | 4/2002 | Akeson et al. | ............. 424/9.32 |
| 6,423,296 B1 | * | 7/2002 | Gunther et al. | .......... 424/9.322 |

* cited by examiner

*Primary Examiner*—Jill Warden
*Assistant Examiner*—Brian Sines
(74) *Attorney, Agent, or Firm*—Burns Doane Swecker & Mathis, L.L.P.

(57) ABSTRACT

A method for improving the magnetic resonance imaging contrast of a selected portion of a sample. A selected ferrimagnetic constituent is associated with the sample portion, by molecular or biological attachment or by some other means, so that the sample portion is distinguished from other adjacent portions of the sample that do not have the selected ferrimagnetic constituent associated therewith. Alternatively, the sample portion is suspected, but not yet confirmed, to have the selected ferrimagnetic constituent associated with it. Ferrimagnetic resonance imaging is performed on the sample portion, and at least one resonance frequency $\omega 0$ of the sample portion is provided. At least one material parameter of the sample portion is measured at or near the frequency $\omega 0$, with enhanced imaging contrast relative to adjacent portions of the sample that do not have the selected ferrimagnetic constituent in association. Alternatively, the measured value is compared with a corresponding reference value for the selected ferrimagnetic constituent. If (and only if) the measured and corresponding reference values substantially agree, the selected ferrimagnetic constituent is present in association with the selected sample portion. Other parameters of the selected ferrimagnetic consituent can also be measured.

20 Claims, 3 Drawing Sheets

MAGNETIC RESONANCE IMAGING CONTRAST SYSTEM

This application is a continuation-in-part (CIP) of U.S. patent application Ser. No. 10/071,563, filed on Feb. 9, 2002, now U.S. Pat. No. 6,693,426 titled "SPATIALLY RESOLVED SPIN RESONANCE DETECTION," the contents of which are herein incorporated by reference.

FIELD OF INVENTION

This invention relates to the novel magnetic resonance imaging contrast mechanism and contrast agents.

BACKGROUND OF THE INVENTION

Magnetic resonance imaging (MRI) techniques have been widely used in a broad range of medical and biological studies and diagnoses. The conventional MRI is based on a mechanism of contrast in relaxation time ($T_2$) for nuclear magnetic resonance of a proton in a biological specimen due to interaction between the proton and any adjacent magnetic contrast agents. The sensitivity of conventional MRI is seriously limited due to the small population differences $\Delta n$ in two adjacent Zeeman levels governed by Boltzmann statistics:

$$\Delta n = 1 - \exp\left(-\frac{h\nu}{kT}\right), \tag{1}$$

where h is Plank's constant, and v is magnetic resonant frequency, which is related to external magnetic field B by the following equation:

$$h\nu = g\,\mu B, \tag{2}$$

where g is gyromagnetic ratio, $\mu$ is the nuclear magneton $\mu_N$ for nuclear magnetic resonance (NMR). At room temperature and in a 5 Tesla magnetic field, this corresponds to a factor of $10^{-5}$ reduction in sensitivity for a typical NMR, and therefore for MRI. Because the mass of an electron is about 1863 times smaller than the mass of a proton, in electron spin resonance (ESR), $\mu$ is replaced by Bohr magnetron $\mu_B$ and the spin population difference is only $10^{-2}$ at room temperature in a 5 Tesla magnetic field. However, the required frequency for electromagnetic radiation to excite the spin resonance, typically 9.8 GHz, is much higher than that of NMR. Radiation having this frequency cannot penetrate deeply and suffers large dielectric loss in a biological specimen, rendering the technique useless in MRI imaging. Recently, many efforts have been made to use lower frequency ESR technique (200 MHz to 3 GHz) for MRI. What is needed is a reliable technique for performing MRI at lower frequencies, preferably no more than 1 GHz.

SUMMARY OF INVENTION

This invention meets this need by using ferromagnetic resonance (FMR) signal as a contrast mechanism for MRI. Ferromagnetic resonance is the electron spin resonance in ferromagnetic or ferrimagnetic media. Due to long-range order of electron spins in ferro- or ferri-magnetic materials, the spin population difference is nearly one at room temperature. As a consequence, the sensitivity of FMR based MRI will not be reduced by the Boltzmann factor at room temperature for spin population difference, even if the radiation frequency is dramatically reduced. Therefore, this approach enables the radio frequency high contrast FMR imaging for biological specimen, human and animal studies/diagnosis. Secondly, the invention selects a specific group of materials or chemicals with specific FMR properties for use in FMR based MRI technique as contrast agents. Ferrimagnetic materials with extremely narrow resonance line width and low dielectric loss will be used for high sensitivity FMR-based-MRI.

DESCRIPTION OF BEST MODES OF THE INVENTION

The importance of narrow resonance linewidth for high near-resonance sensitivity is seen in both the real and imaginary parts of the complex permeability $\mu = \mu' - j\mu''$. In microwave circuits, $\mu'$ controls the signal phase and $\mu''$ the energy absorption or circuit Q factor. Their relations as a function of angular frequency $\omega$ can be expressed as $$\mu' = 1 + \frac{\gamma 4\pi M(\omega - \omega_0)}{(\omega^2 - \omega_0^2) + \gamma^2 (\Delta H)^2} \tag{3a}$$

$$\approx 1 + \frac{\gamma 4\pi M(\omega - \omega_0)}{\gamma^2 (\Delta H)^2} \text{(near resonance) and}$$

$$\mu'' = 1 + \frac{\gamma 4\pi M(\omega - \omega_0)}{(\omega^2 - \omega_0^2) + \gamma^2 (\Delta H)^2} \tag{3b}$$

$$\approx 1 + \frac{4\pi M}{\Delta H} \text{(at resonance)}$$

where $4\pi M$ is the magnetization comprising the volume density of individual magnetic moments m, $\omega_0$ is the resonance frequency, and $\Delta H$ is the Q factor half-linewidth. The factor $\gamma$ is the gyromagnetic constant and is derived from the Larmor precession relation between frequency and field, given by $$\omega_0 = \gamma H = \frac{g|e|}{2\,\text{mc}} H, \tag{4}$$

where $\gamma$ is the gyromagnetic constant, e is the electron or proton charge, m is the particle mass and c is the velocity of light, and g (~2 for spins) is the spectroscopic splitting factor. Note that e is the same magnitude for both protons and electrons, but $m_n$ for protons is greater than $m_e$ for electrons by a factor 1836, thereby reducing the resonance frequency by a factor of more than $10^3$ for a given magnetic field intensity H. This difference in mass has implications beyond the size of $\gamma$: the individual magnetic moment of an electron spin (Bohr magneton) and proton spin (nuclear magneton) are affected in the same proportion, according to $$\text{Electron Bohr magneton, } m_B = \frac{|e|\hbar}{2m_e c} \tag{5}$$

$$\text{Nuclear magneton, } m_n = \frac{|e|\hbar}{2m_n c}.$$

Gyromagnetic resonance occurs in specimens that are paramagnetic from dispersed individual nuclear (NMR) or electron (EPR) magnetic moments, and ferromagnetic (FMR) in high density electron systems where magnetic exchange can dominate. The principal differences between these specimens in the application of Eq. (1) are: the magnitude of M and its variation with temperature, the microwave damping or relaxation mechanism that determines the half-linewidth ΔH, and the magnetic field condition that determines the resonance frequency $\omega_0$.

Magnitude of 4 πM

Figure 1:
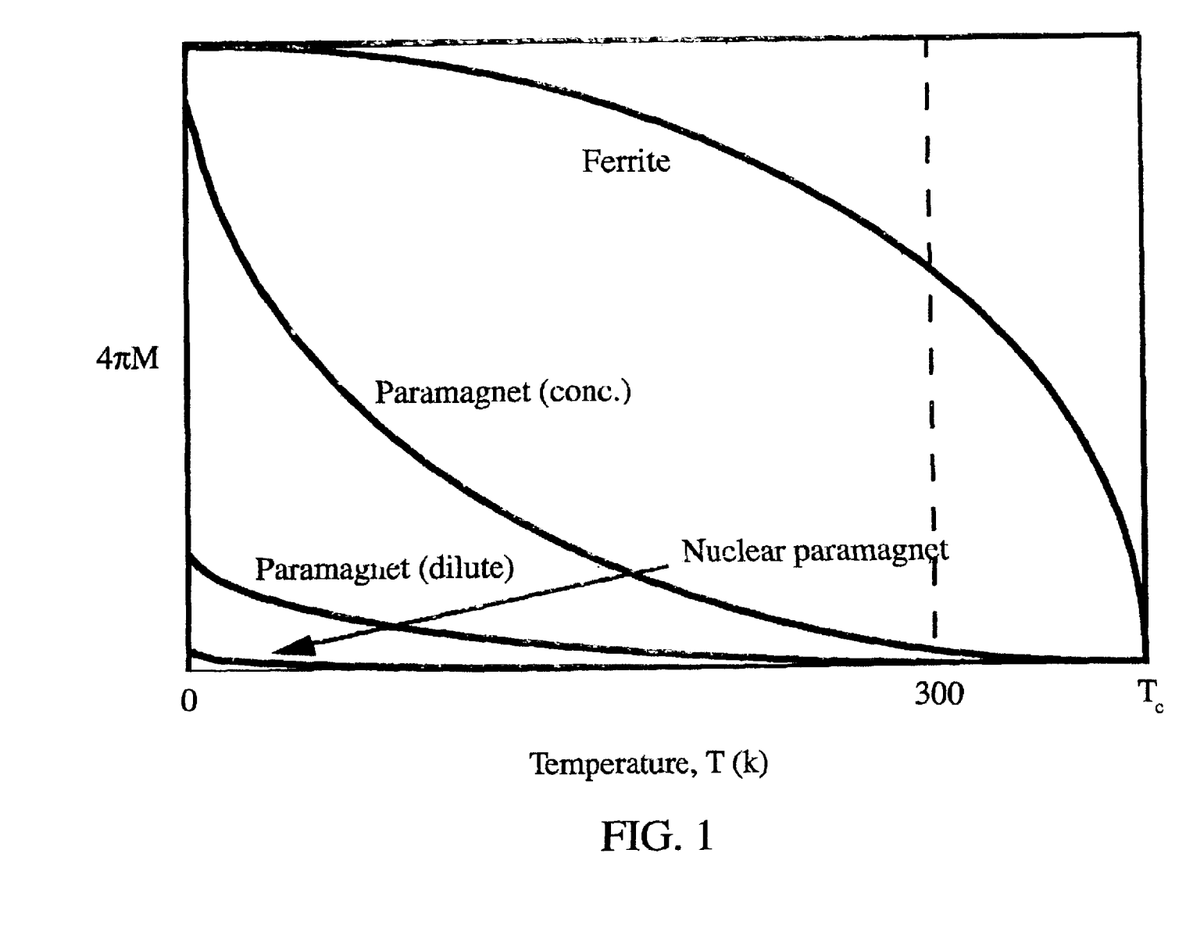
FIG. 1 illustrates a Brillouin function for varying temperatures in a fixed magnetic field for several materials.

The strength of M is clearly tied to the density of magnetic moments, but it is equally dependent on the degree of alignment, which is proportional to the dc susceptibility in paramagnetism. From the Langevin and Brillouin classical models of magnetism, one verifies that spin concentrated paramagnetic systems can achieve high alignment only at the lowest temperatures and that the decline of M accelerates with the increase in temperature to reach extremely low values by room temperature because of the small value of the ratio $\mu H/kT$. For this reason, neither nuclear nor electronic paramagnetism has found much use beyond that of probing materials for studying their atomic-scale properties. With ferro- or ferrimagnetic specimens, the magnetic models are easier to deal with, because the enormous fixed exchange field $H_{ex}$ (~$10^2$ to $10^3$ Tesla) dictates near-optimum spin alignment of the undiluted moments through the critical parameter $mH_{ex}/kT$, which remains large up to temperatures approaching the Curie point threshold, as illustrated qualitatively in FIG. 1. Therefore, ferromagnetic resonance (FMR) sensitivity benefits greatly from both higher moment density and greater alignment.

Origin of ΔH

Several factors contribute to the linewidth, chief among which are (1) spin-lattice interactions of individual spins, characterized by a relaxation time $\tau_1$, and (2) incoherent precessional phasing of spins, characterized by a relaxation time $\tau_2$ that arises from misaligned spins coupled by dipolar interactions. Precession phase decoherence can also occur in exchange ordered electron spin systems by spin wave generation, particularly in higher power cases where crystal imperfections or nonuniform rf fields exist in a specimen having dimensions greater than the wavelength of the rf signal. These mechanisms are generally considered to be homogeneous and produce a Lorentzian line shape.

Inhomogeneities can cause severe broadening by creating local regions of different resonance frequencies in a Gaussian-type distribution. Most common among these cases are polycrystalline ferromagnetic specimens with crystal grains of random crystallographic orientation with varying magnetic anisotropy bias fields and structural inhomogeneities such as nonmagnetic phases, porosity and grain boundaries that can broaden the effective ΔH of a typical ferrite by more than a hundred oersteds. In small specimens with rough surfaces, demagnetization effects on linewidth, similar to those of bulk porosity, have been observed. For this reason, the discussion of FMR that follows focuses on highly polished single crystal specimens where only the homogeneous broadening effects from the relaxation rates $\tau_1^{-1}$ and $\tau_2^{-1}$.

For homogeneous relaxation broadening, $$\Delta H = (\gamma \tau)^{-1}, \tag{6}$$

where the relaxation time $\tau$ can be a resultant of both $\tau_1$ and $\tau_2$ contributions, but is generally dominated by only one of them. Relaxation rates of paramagnetic systems are influenced primarily by $\tau_2^{-1}$, with the possible exception of certain electron cases where fast relaxing ions allow two-phonon Raman processes to render $\tau_1^{-1}$ large enough to approach or exceed $\tau_2^{-1}$. With ferromagnetic specimens, the spin-spin relaxation rate in ideal situations is effectively zero because of complete spin alignment means perfect precessional phase coherence. Although $\tau_1^{-1}$ becomes the dominant relaxation parameter, only selected ions can fulfill the goal of narrow linewidth. Estimated values of these parameters are listed in Table 1 for typical situations.

Shape Anisotropy of $\omega_0$

The resonance frequency $\omega_0$ can vary with orientation of the specimen in different ways. For paramagnets, γ can be sensitive to crystallographic direction, and in some case, range widely. However, γ is relatively isotropic in ferrimagnets with $d^5$ or $d^7$ magnetic ions The main sources of anisotropy come from surface poles that induce demagnetizing fields proportional to 4 πM inside the specimen, and from fields proportional to ratio of the magnetocrystalline anisotropy fields that are associated with specific crystallographic axes.

For a fully magnetized ellipsoidal specimen with H and M aligned with the z-axis, the resonance frequency is expressed as $$\omega_0 = \gamma H_i, \tag{7}$$

where the internal field for resonance is given by $$H_x = \left\{ \begin{array}{l} [H + (H_{Kx} - H_{Ks}) + (N_{Dx} - N_{Dz})4\pi M] \times \\ [H + (H_{Ky} - H_{Kz}) + (N_{Dy} - N_{Dz})4\pi M] \end{array} \right\}^{\frac{1}{2}}. \tag{8}$$

The subscripts x and y refer to the two axes of the ellipsoid that are orthogonal to the z direction of H in the coordinate system selected. Note that $H_i$ reduces to the applied field H when all of the demagnetizing factors are zero.

For resonance to occur with H along the z-axis, $H_{rf}$ must have a component in the xy-plane, but values of the $H_K$ anisotropy fields and the $N_D$ factors will be sensitive to the direction of H within the plane. Applied to the limiting case of a thin flat plate with $N_{Dx}=1$, and $N_{Dy}$, $N_{Dz}=0$, and $H_K$ terms ignored, Eq. (6) simplifies to $$\omega_0 = \gamma [H(H+4\pi M)]^{1/2} \ (H \text{ in plane})$$

$$\omega_0 = \gamma (H-4\pi M) \ (H \text{ normal to plane}) \tag{9}$$

For a long slender cylinder (acicular particle) aligned with the z-axis, $N_{Dx}$, $N_{Dy}=\frac{1}{2}$, and $N_{Dz}=0$. The resonance frequency is then $$\omega_0 = \gamma (H+2\pi M) \ (H \text{ parallel to long axis})$$

$$\omega_0 = \gamma [H(H-2\pi M)]^{1/2} \ (H \text{ normal to long axis}) \tag{10}$$

For a sphere, $N_{Dx}=N_{Dy}=N_{Dz}=\frac{1}{3}$, and the shape demagnetizing factors cancel, so that $H_i=H$.

$$\omega_0 = \gamma H. \tag{11}$$

As a consequence, care must be taken in selecting specimen shapes. If groups or assemblies of identical particles are examined within the same sample volume, geometric orientations must also be identical to avoid inhomogeneous line broadening. From Eq. (9), it is clear that spherical particles are most suitable for this purpose. In addition, dispersal of the individual ferrimagnets is also important to avoid dipolar interactions on a macroscopic scale, e.g., superparamagnetism.

Magnetocrystalline Anisotropy of $\omega_0$

Because the effect on the resonance condition from anisotropy fields also varies with crystallographic orientation, the $H_K$ terms remain important even when spherical shapes are involved. For randomly oriented crystallites in ceramics, variable $H_K$ values serve to produce inhomogeneous broadening of the FMR lines of ceramic ferrites. For a single crystal sphere of cubic symmetry magnetized to saturation along a specific crystallographic axis, the FMR frequency is expressed as $$\omega_0 = \gamma\left(H + \frac{2K_1}{M}\right) \quad (H\|\langle 100\rangle\text{direction}) \quad (12)$$

$$\omega_0 = \gamma\left[\left(H + \frac{K_1}{M} - \frac{K_2}{18M}\right)\left(H + \frac{K_2}{3M}\right)\right]^{\frac{1}{2}} \quad (H\|\langle 112\rangle\text{direction})$$

$$\omega_0 = \gamma\left(H - \frac{4}{3}\frac{K_1}{M} - \frac{4}{9}\frac{K_2}{2M}\right) \quad (H\|\langle 111\rangle\text{direction})$$

$$\omega_0 = \gamma\left[\left(H - \frac{2K_1}{M}\right)\left(H + \frac{K_1}{M} - \frac{K_2}{2M}\right)\right]^{\frac{1}{2}} \quad (H\|\langle 110\rangle\text{direction}),$$

where $K_1$ and $K_2$ are the first- and second-order magnetocrystaline anisotropy constants. Thus, the location of the resonance line in frequency space for spheres will vary with chemical composition according to the respective $K_1/M$ and $K_2/M$ terms, while preserving the desired sensitivity of $\mu''$ gained from the small $\Delta H$ values.

Conclusions

Nuclear magnetism is limited by the low value of the nuclear magneton (the strength of the proton magnetic moment), which is smaller than the electron Bohr magneton by the ratio 1836 of the respective particle masses. For resonance effects, however, the nuclear systems have the advantage of very long $\tau_1$ and $\tau_2$ values because of the absence of spin-orbit coupling and the relative lack of dipole-dipole interaction between neighboring nuclei. From a practical standpoint, the major disadvantage of nuclear magnetic resonance is the magnet requirement to supply highly uniform magnetic fields of kOe magnitude sufficient to establish resonance frequencies large enough to reduce wavelengths to practical dimensions, i.e., in the kHz to MHz range. Electron paramagnetism offers larger individual magnetic moments, but unfortunately has broader associated linewidths resulting from relaxation times that are shortened by spin-orbit coupling in all cases except the half-filled shell ions, i.e., $3d^5$ of $Fe^{3+}$, $Mn^{2+}$ or rare earth $4f^7$ of $Gd^{3+}$, $Eu^{2+}$. Strong dipolar coupling also reduces $\tau_2$ when concentrations of paramagnetic centers are increased in attempts to raise the dc susceptibility.

For collection of particles, single-crystal ferromagnetic spheres offer clear advantages of high detectability through large magnetizations and narrow FMR lines. Because the resonance frequency can vary by tens of oersteds as a function of $H_K$, when particles of different chemical composition are used. For example, yttrium-iron garnet $Y_3Fe_5O_{12}$ with varying amounts of magnetic dilution can be spectrally stored by FMR frequency. Magnetic garnets and spinels are also chemically inert and indestructible under normal environmental conditions.

A comprehensive list of potential dilutant ions for the generic $\{c\}_3(a)_2[d]_3O_{12}$ and spinel $A[B]_2O_4$ ferrite compounds that could produce different $\omega_0$ values while preserving the narrow $\Delta H$ requirement is presented in Table 2. Among those ions to be avoided are those with fast spin-lattice relaxation rates, specifically members of the 3d or 4f transition series without half-filled shells, particularly $Co^{2+}$, $Fe^{2+}$, or any of the lanthanide (rate earth) series not listed in Table 2.

The invention relies upon realizations that: (1) FMR has a higher spin population difference, and greater sensitivity or contrast, than the corresponding differences for NMR and EPR by factors of approximately $10^5$ and $10^2$, respectively; (2) use of a ferrimagnetic, as opposed to use of a ferromagnetic material as a contrast-enhancing sample "tag" provides much narrower linewidths, and thus much greater corresponding relaxation times, for imaging of a selected portion of a sample. -What one seeks in use of a ferrimagnetic material in an FMR procedure are longer relaxation times, narrow frequency linewidths, higher peak output signals at resonance, a higher signal-to-noise ratio (SNR), and increased flexibility in location of a selected sample portion chosen for interrogation.

Figure 2A:
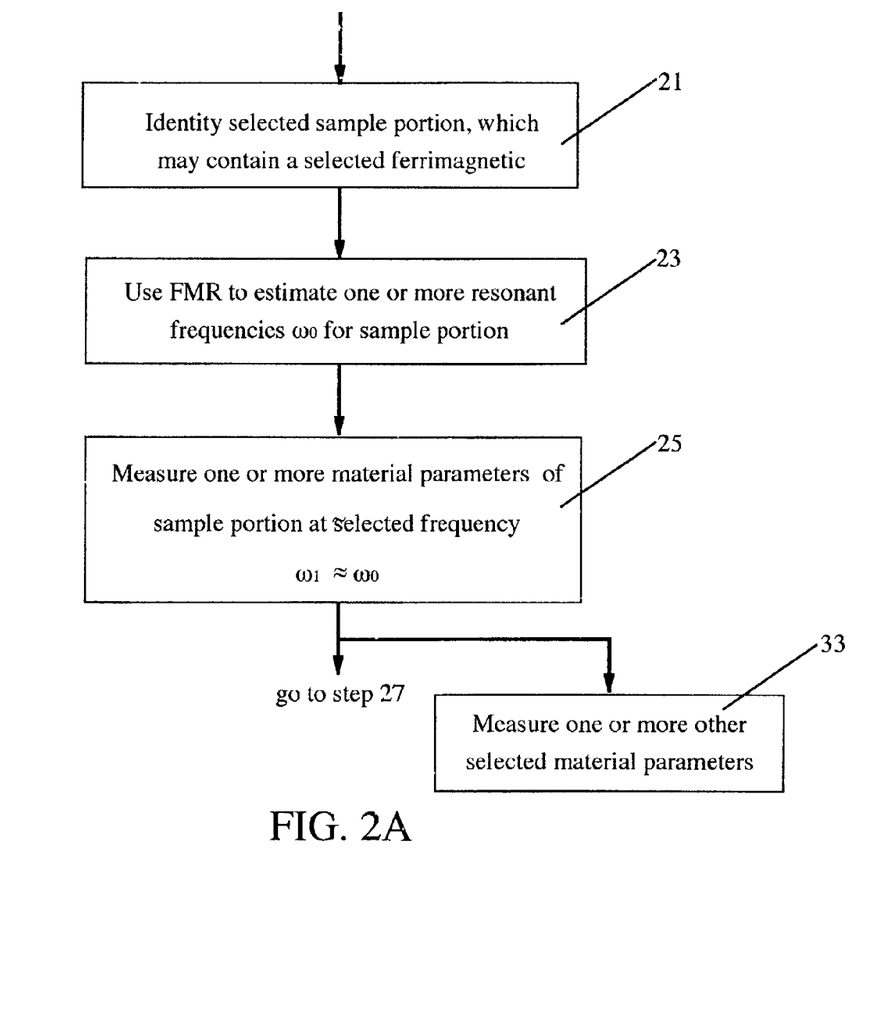
FIG. 2 is a flow chart of a procedure for practising the invention.
Figure 2B:
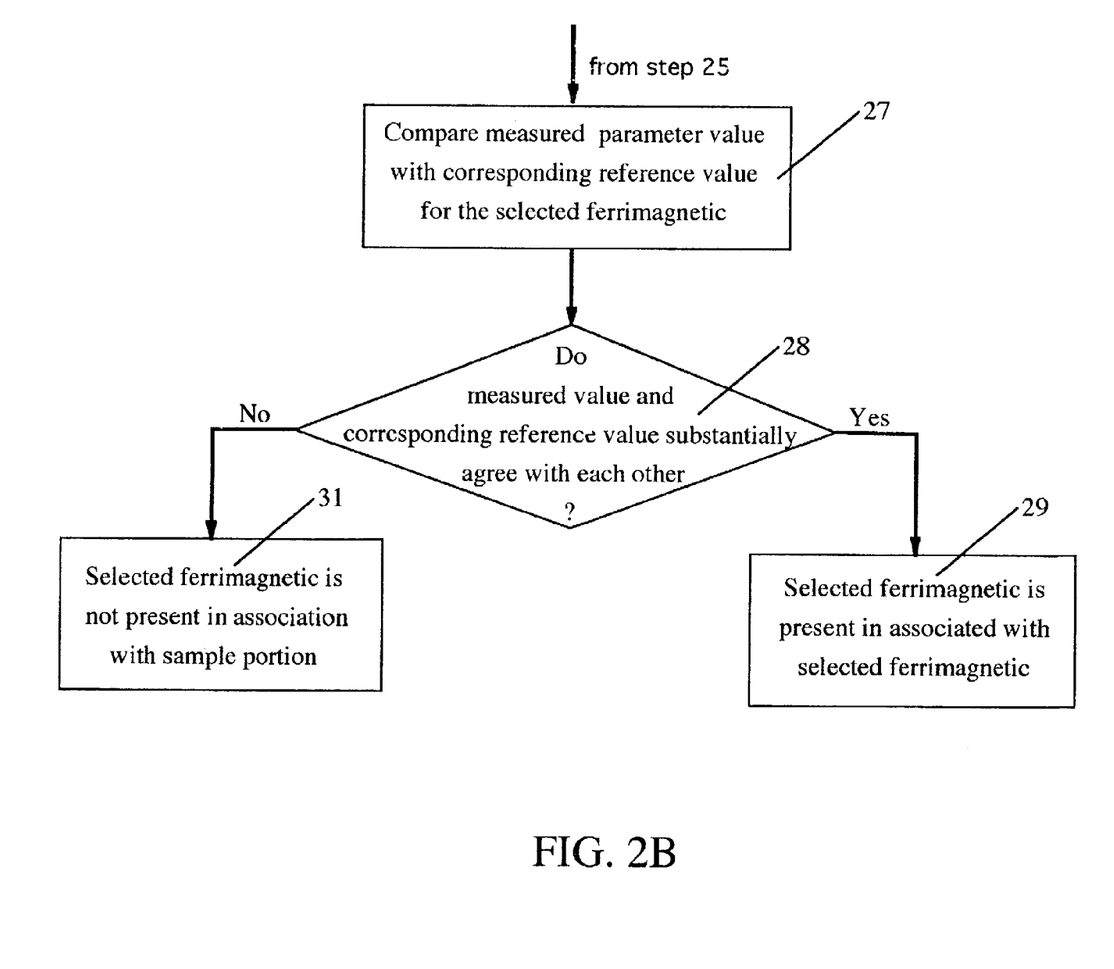

FIG. 2 illustrates a flow chart for a procedure for practicing the invention. In step 21, a selected sample portion, which is suspected to have associated with the sample portion at least one selected ferrimagnetic constituent, is identified for interrogation. This sample portion may be a pure ferrimagnetic constituent or may be another sample that is "tagged" with a ferrimagnetic constituent, through selective association or molecular or biological attachment. In step 23, the sample portion is interrogated, using an NMR or EPR procedure adapted for use in FMR, to estimate one or more resonant frequencies $\omega_0$ for the sample portion. A suitable NMR experimental method is described in N. Bloembergen, *Nuclear Magnetic Relaxation*, W. A. Benjamin Publ., 1961, pp. 52–81. Generally, an excitation magnetic field, at a frequency $\omega=\omega 1\approx\omega 0$, plus a gradient external magnetic field are applied, each field optionally having a static component and a time varying component. In step 25, a measurement at at least one frequency $\omega_1$ resonant is used to determine one or more selected material parameters, such as $\mu'(\omega_1)$ or $\mu''(\omega_1)$, for the sample portion, at one or more (preferably two or more) selected locations. At each of the selected locations, the gradient external magnetic field strength is adjusted, or the sample portion is moved and the external field is kept unchanged, to provide a selected external magnetic field strength at the selected location.

In steps 27 and 28, the value of the measured parameter value is compared with a corresponding reference parameter value for the selected ferrimagnetic constituent. If the compared values substantially agree (e.g., are within a few percent of each other), this condition is interpreted as indicating that the selected ferrimagnetic constituent is present, in association with the sample portion, in step 29. For added confidence that the selected ferrimagnetic constituent is present, comparison of a measured parameter value and a corresponding reference parameter value may be made for each of two or more parameters. If the compared values do not substantially agree, this condition is interpreted as indicating that the selected ferrimagnetic constituent is not associated with the sample portion, in step 31 (optional).

By identifying within the sample portion a suitable set of two or more selected measurement locations, each associated with the selected ferrimagnetic constituent, the sample portion can be imaged. If material, adjacent to but not part of the sample portion, does not have the selected ferrimagnetic constituent in association therewith, the imaging contrast of the sample portion is enhanced, relative to the adjacent material, based upon agreement of non-agreement of the measured and corresponding reference values.

If the primary goal is to provide a sample portion with increased contrast for imaging, the procedure may stop here. If the primary goal is to provide measurements of one or more additional parameters, such as magnetization $M(\omega_1)$, linewidth(s), relaxation time(s), magnetic anisotropy of $\omega_0$, shape anisotropy of $\omega_0$, and peak signal at resonance, these measurements are made in step 33.

The size or volume of the portion of the sample selected for imaging will be determined by the characteristics of the FMR imaging procedure used.

TABLE 1

Estimates of gyromagnetic resonance parameters at T = 300° K.

| | $4\pi M$ G | $\tau_1$ sec | $\tau_2$ sec | $\Delta H$ Oe | $\mu''$ |
|---|---|---|---|---|---|
| NMR | ~2 (conc.) | >$10^4$ | ~$10^{-4}$ | ~0.05 | ~40 |
| EPR ($Fe^{3+}$) | 20 (dilute) | >$10^{-6}$ | ~$10^{-7}$ | ~5 | ~4 |
| | 2000 (conc.) | | ~$10^{-9}$ | ~500 | ~4 |
| FMR ($Fe^{3+}$) | 2000 (conc.) | >$10^{-6}$ | → | <0.5 | 4000 |

TABLE 2

Ferrite dilution ions for preserving narrow linewidth.

| Garnet $\{c\}_3(a)_2[d]_3O_{12}$ | | Spinel $A[B]_2O_4$ | |
|---|---|---|---|
| {c} dodecahedral | (a) octahedral [d] tetrahedral | A tetrahedral | [B] octahedral |
| $Y^{3+}$ (highest purity) | $Fe^{3+}$ | $Fe^{3+}$ | $Fe^{3+}$ |
| $La^{3+}$ (highest purity) | $Mn^{2+}$ | $Mn^{2+}$ | $Mn^{2+}$ |
| $Gd^{3+}$ (highest purity) | $Ru^{3+}$ | $Ru^{3+}$ | $Ru^{3+}$ |
| $Eu^{2+}$ (highest purity) | $Cu^{1+}$ | $Cu^{1+}$ | $Cu^{1+}$ |
| $Na^{1+}$ | $V^{3+}$ [d], $Ni^{2+}$ (a) | $V^{3+}$ | $Ni^{2+}$ |
| $K^{1+}$ | $Cr^{4+}$ [d], $Cu^{3+}$ (a) | $Cr^{4+}$ | $Cu^{3+}$ |
| $Rb^{1+}$ | $Mo^{4+}$ [d], $Cr^{3+}$ (a) | $Mo^{4+}$ | $Cr^{3+}$ |
| $Tl^{1+}$ | $W^{4+}$ [d], $Mo^{3+}$ (a) | $W^{4+}$ | $Mo^{3+}$ |
| $Ag^{1+}$ | $Nb^{3+}$ [d], $W^{3+}$ (a) | $Nb^{3+}$ | $W^{3+}$ |
| $Au^{1+}$ | $Zn^{2+}$ | $Zn^{2+}$ | $Zn^{2+}$ |
| $Hg^{1+}$ | $Mg^{2+}$ | $Mg^{2+}$ | $Mg^{2+}$ |
| $Ca^{2+}$ | $Al^{3+}$ | $Al^{3+}$ | $Al^{3+}$ |
| $Sr^{2+}$ | $Ga^{3+}$ | $Ga^{3+}$ | $Ga^{3+}$ |
| $Ba^{2+}$ | $In^{3+}$ | $In^{3+}$ | $In^{3+}$ |
| $Hg^{2+}$ | $Sc^{3+}$ | $Sc^{3+}$ | $Sc^{3+}$ |
| $Pb^{2+}$ | $Ti^{4+}$ | $Ti^{4+}$ | $Ti^{4+}$ |
| $Bi^{3+}$ | $Zr^{4+}$ | $Zr^{4+}$ | $Zr^{4+}$ |
| $In^{3+}$ | $Hf^{4+}$ | $Hf^{4+}$ | $Hf^{4+}$ |
| $Sc^{3+}$ | $Si^{4+}$ | $Si^{4+}$ | $Si^{4+}$ |
| | $Ge^{4+}$ | $Ge^{4+}$ | $Ge^{4+}$ |
| | $Sn^{4+}$ | $Sn^{4+}$ | $Sn^{4+}$ |
| | $V^{5+}$ | $V^{5+}$ | $V^{5+}$ |
| | $Nb^{5+}$ | $Nb^{5+}$ | $Nb^{5+}$ |
| | $Ta^{5+}$ | $Ta^{5+}$ | $Ta^{5+}$ |
| | $P^{5+}$ | $P^{5+}$ | $P^{5+}$ |
| | $As^{5+}$ | $As^{5+}$ | $As^{5+}$ |
| | $Sb^{5+}$ | $Sb^{5+}$ | $Sb^{5+}$ |

What is claimed is:

1. A method for performing magnetic resonance imaging on a selected portion of a sample, the method comprising:

providing a selected ferrimagnetic material into the sample by chemically bonding the ferrimagnetic material in particle format to the sample, the ferrimagnetic material having known ferromagnetic spin resonance characteristics, at least one resonant frequency $\omega=\omega 0$, and a diameter no greater than 1 $\mu$m, the ferrimagnetic material now a constituent of a selected portion of the sample;

applying an excitation electromagnetic field to the sample using an electromagnetic wave generator, the excitation electromagnetic field having at least one of a static component and a time varying component with a frequency $\omega=\omega 1 \approx \omega 0$, a selected magnetic field strength, and a selected magnetic field direction relative to the sample portion;

applying an external gradient magnetic field to the sample, the external gradient magnetic field having at least one of a static component and a time varying component, a selected magnetic field direction, and at least first and second selected magnetic field strengths at at least first and second selected locations, respectively, within the sample portion;

measuring at or near the resonant frequency $\omega 0$ of the ferrimagnetic material at least one of (i) a real component $\mu'(\omega')$ of the complex permeability parameter, and (ii) an imaginary component $\mu''(\omega 1)$ of the complex permeability parameter of the sample portion at each of the selected locations to determine at least one value of a material parameter at each of the selected locations; and constructing an image of the sample portion, by comparing the measured parameter values with corresponding reference values for the selected ferrimagnetic constituent for each of the selected locations.

2. The method of claim 1, further comprising:

comparing at least one of said measured parameter values for each of said selected locations with said corresponding reference value for said selected ferrimagnetic constituent; and when said measured value and said corresponding reference value substantially agree, interpreting this condition as indicating that said selected ferrimagnetic constituent is associated with the sample portion at said selected location at which said material parameter measurement is taken.

3. The method of claim 1, further comprising:

when said measured value and said corresponding reference value do not substantially agree, interpreting this condition as indicating that said selected ferrimagnetic constituent is not associated with said sample portion at said selected location at which said material parameter measurement is taken.

4. A method for performing magnetic resonance imaging on a selected portion of a sample, the method comprising:

providing a selected ferrimagnetic material into the sample by chemically bonding the ferrimagnetic material in particle format to the sample, the ferrimagnetic material having known ferromagnetic spin resonance characteristics, at least one resonant frequency $\omega=\omega 0$, and a diameter no greater than 1 $\mu$m, the ferrimagnetic material now a constituent of a selected portion of the sample;

applying an excitation electromagnetic field to the sample using an electromagnetic wave generator, the excitation electromagnetic field having at least one of a static component and a time varying component with a frequency $\omega=\omega 1 \approx \omega 0$, a selected magnetic field strength, and a selected magnetic field direction relative to the sample portion;

applying an external gradient magnetic field to the sample, the external gradient magnetic field having at least one of a static component and a time varying component, a selected magnetic field direction, and at least first and second selected magnetic field strengths at at least first and second selected locations, respectively, within the sample portion;

measuring at or near the resonant frequency $\omega 0$ of the ferrimagnetic material at least one of (i) a real component $\mu'(\omega 1)$ of the complex permeability parameter, and (ii) an imaginary component $\mu''(\omega 1)$ of the complex permeability parameter of the sample portion at each of the selected locations to determine at least one value of a material parameter at each of the selected locations; and constructing an image of the sample portion, by comparing the measured parameter values with corresponding reference values for the selected ferrimagnetic constituent for each of the selected locations;

the method further comprising choosing said selected ferrimagnetic constituent from a group of ferrimagnetic compounds consisting of a compound $\{c\}_3(a)_2[d]_3O_{12}$, where $\{c\}$ is in dodecahedral form, (a) is in octrahedral form, [d] is in tetrahedral form and the element c is drawn from a group consisting of $Na^{1+}$, $K^{1+}$, $Rb^{1+}$, $Tl^{1+}$, $Ag^{1+}$, $Au^{1+}$, $Hg^{1+}$, $Eu^{2+}$, $Ca^{2+}$, $Sr^{2+}$, $Ba^{2+}$, $Hg^{2+}$, $Pb^{2+}$, $Y^{3+}$, $La^{3+}$, $Gd^{3+}$, $Bi^{3+}$, $In^{3+}$ and $Sc^{3+}$.

5. A method for performing magnetic resonance imagine on a selected portion of a sample, the method comprising:

providing a selected ferrimagnetic material into the sample by chemically bonding the ferrimagnetic material in particle format to the sample, the ferrimagnetic material having known ferromagnetic spin resonance characteristics, at least one resonant frequency $\omega=\omega 0$, and a diameter no greater than 1 $\mu$m, the ferrimagnetic material now a constituent of a selected portion of the sample;

applying an excitation electromagnetic field to the sample using an electromagnetic wave generator, the excitation electromagnetic field having at least one of a static component and a time varying component with a frequency $\omega=\omega 1 \approx \omega 0$, a selected magnetic field strength, and a selected magnetic field direction relative to the sample portion;

applying an external gradient magnetic field to the sample, the external gradient magnetic field having at least one of a static component and a time varying component, a selected magnetic field direction, and at least first and second selected magnetic field strengths at at least first and second selected locations, respectively, within the sample portion;

measuring at or near the resonant frequency $\omega 0$ of the ferrimagnetic material at least one of (i) a real component $\mu'(\omega 1)$ of the complex permeability parameter, and (ii) an imaginary component $\mu''(\omega 1)$ of the complex permeability parameter of the sample portion at each of the selected locations to determine at least one value of a material parameter at each of the selected locations; and constructing an image of the sample portion, by comparing the measured parameter values with corresponding reference values for the selected ferrimagnetic constituent for each of the selected locations;

the method further comprising choosing said selected ferrimagnetic constituent from a group of ferrimagnetic compounds consisting of a compound $\{c\}_3(a)_2[d]_3O_{12}$, where $\{c\}$ is in dodecahedral form, (a) is in octrahedral form, [d] is in tetrahedral form and the element a is drawn from a group consisting of $Cu^{1+}$, $Mn^{2+}$, $Ni^{2+}$, $Zn^{2+}$, $Mg^{2+}$, $Fe^{3+}$, $Ru^{3+}$, $Cu^{3+}$, $Cr^{3+}$, $Mo^{3+}$, $W^{3+}$, $Al^{3+}$, $Ga^{3+}$, $In^{3+}$, $Sc^{3+}$, $Ti^{4+}$, $Z^{4+}$, $Hf^{4+}$, $Si^{4+}$, $Ge^{4+}$, $Sn^{4+}$, $V^{5+}$, $Nb^{5+}$, $Ta^{5+}$, $P^{5+}$, $As^{5+}$, and $Sb^{5+}$.

6. A method for performing magnetic resonance imagine on a selected portion of a sample, the method comprising:

providing a selected ferrimagnetic material into the sample by chemically bonding the ferrimagnetic material in particle format to the sample, the ferrimagnetic material having known ferromagnetic spin resonance characteristics, at least one resonant frequency $\omega=\omega 0$, and a diameter no greater than 1 $\mu$m, the ferrimagnetic material now a constituent of a selected portion of the sample;

applying an excitation electromagnetic field to the sample using an electromagnetic wave generator, the excitation electromagnetic field having at least one of a static component and a time varying component with a freguency $\omega 32 \omega 1 \approx \omega 0$, a selected magnetic field strength, and a selected magnetic field direction relative to the sample portion;

applying an external gradient magnetic field to the sample, the external gradient magnetic field having at least one of a static component and a time varying component, a selected magnetic field direction, and at least first and second selected magnetic field strengths at at least first and second selected locations, respectively, within the sample portion;

measuring at or near the resonant frequency $\omega 0$ of the ferrimagnetic material at least one of (i) a real component $\mu'(\omega 1)$ of the complex permeability parameter, and (ii) an imaginary component $\mu''(\omega 1)$ of the complex permeability parameter of the sample portion at each of the selected locations to determine at least one value of a material parameter at each of the selected locations; and constructing an image of the sample portion, by comparing the measured parameter values with corresponding reference values for the selected ferrimagnetic constituent for each of the selected locations;

the method further comprising choosing said selected ferrimagnetic constituent from a group of ferrimagnetic compounds consisting of a compound $\{c\}_3(a)_2[d]_3O_{12}$, where $\{c\}$ is in dodecahedral form, (a) is in octrahedral form, [d] is in tetrahedral form and the element d is drawn from a group consisting of $Cu^{1+}$, Mn2+, $Ni^{2+}$, $Zn^{2+}$, $Mg^{2+}$, $Fe^{3+}$, $Ru^{3+}$, $V^{3+}$, $Nb^{3+}$, $Al^{3+}$, $Ga^{3+}$, $In^{3+}$, $Sc^{3+}$, $Cr^{4+}$, $Mo^{4+}$, $W^{4+}$, $Ti^{4+}$, $Zr^{4+}$, $Hf^{4+}$, $Si^{4+}$, $Ge^{4+}$, $Sn^{4+}$, $V^{5+}$, $Nb^{5+}$, $Ta^{5+}$, $P^{5+}$, $As^{5+}$, and $Sb^{5+}$.

7. The method of claim 1, A method for performing magnetic resonance imaging on a selected portion of a sample, the method comprising:

providing a selected ferrimagnetic material into the sample by chemically bonding the ferrimagnetic material in particle format to the sample, the ferrimagnetic material having known ferromagnetic spin resonance characteristics, at least one resonant frequency $\omega=\omega 0$, and a diameter no greater than 1 $\mu$m, the ferrimagnetic material now a constituent of a selected portion of the sample;

applying an excitation electromagnetic field to the sample using an electromagnetic wave generator, the excitation electromagnetic field having at least one of a static component and a time varying component with a frequency $\omega=\omega 1 \approx \omega 0$, a selected magnetic field strength, and a selected magnetic field direction relative to the sample portion;

applying an external gradient magnetic field to the sample, the external gradient magnetic field having at least one of a static component and a time varying component, a selected magnetic field direction, and at least first and second selected magnetic field strengths at at least first and second selected locations, respectively, within the sample portion;

measuring at or near the resonant frequency $\omega 0$ of the ferrimagnetic material at least one of (i) a real component $\mu'(\omega 1)$ of the complex permeability parameter, and (ii) an imaginary component $\mu''(\omega 1)$ of the complex permeability parameter of the sample portion at each of the selected locations to determine at least one value of a material parameter at each of the selected locations; and constructing an image of the sample portion, by comparing the measured parameter values with corresponding reference values for the selected ferrimagnetic constituent for each of the selected locations;

the method further comprising choosing said selected ferrimagnetic constituent from a group of ferrimagnetic compounds consisting of a compound $A[B]_2O_4$, where A is in tetrahedral form, B is in octahedral form, and the element A is drawn from a group consisting of $Cu^{1+}$, $Mn^{2+}$, $Ni^{2+}$, $Mg^{2+}$, $Zn^{2+}$, $Fe^{3+}$, $Ru^{3+}$, $V^{3+}$, $Nb^{3+}$, $Al^{3+}$, $Ga^{3+}$, $In^{3+}$, $Sc^{3+}$, $Cr^{4+}$, $Mo^{4+}$, $W^{4+}$, $Ti^{4+}$, $Zr^{4+}$, $Hf^{4+}$, $Si^{4+}$, $Ge^{4+}$, $Sn^{4+}$, $V^{5+}$, $Nb^{5+}$, $Ta^{5+}$, $P^{5+}$, $As^{5+}$, and $Sb^{5+}$.

8. A method for performing magnetic resonance imaging on a selected portion of a sample, the method comprising:

providing a selected ferrimagnetic material into the sample by chemically bonding the ferrimagnetic material in particle format to the sample, the ferrimagnetic material having known ferromagnetic spin resonance characteristics, at least one resonant frequency $\omega=\omega 0$, and a diameter no greater than 1 $\mu$m, the ferrimagnetic material now a constituent of a selected portion of the sample;

applying an excitation electromagnetic field to the sample using an electromagnetic wave generator, the excitation electromagnetic field having at least one of a static component and a time varying component with a frequency $\omega=\omega 1 \approx \omega 0$, a selected magnetic field strength, and a selected magnetic field direction relative to the sample portion;

applying an external gradient magnetic field to the sample, the external gradient magnetic field having at least one of a static component and a time varying component, a selected magnetic field direction, and at least first and second selected magnetic field strengths at at least first and second selected locations, respectively, within the sample portion;

measuring at or near the resonant frequency $\omega 0$ of the ferrimagnetic material at least one of (i) a real component $\mu'(\omega 1)$ of the complex permeability parameter, and (ii) an imaginary component $\mu''(\omega 1)$ of the complex permeability parameter of the sample portion at each of the selected locations to determine at least one value of a material parameter at each of the selected locations; and constructing an image of the sample portion, by comparing the measured parameter values with corresponding reference values for the selected ferrimagnetic constituent for each of the selected locations;

the method further comprising choosing said selected ferrimagnetic constituent from a group of ferrimagnetic compounds consisting of a compound $A[B]_2O_4$, where A is in tetrahedral form, B is in octahedral form, and the element B is drawn from a group consisting of $Cu^{1+}$, $Mn^{2+}$, $Ni^{2+}$, $Mg^{2+}$, $Zn^{2+}$, $Fe^{3+}$, $Ru^{3+}$, $V^{3+}$, $Nb^{3+}$, $Al^{3+}$, $Ga^{3+}$, $In^{3+}$, $Sc^{3+}$, $Cr^{4+}$, $Mo^{4+}$, $W^{4+}$, $Ti^{4+}$, $Zr^{4+}$, $Hf^{4+}$, $Si^{4+}$, $Ge^{4+}$, $Sn^{4+}$, $V^{5+}$, $Nb^{5+}$, $Ta^{5+}$, $P^{5+}$, $As^{5+}$, and $Sb^{5+}$.

9. The method of claim 1, further comprising choosing said measured material parameter value from the following group of parameter values: said at least one location of said ferrimagnetic constituent, output signal amplitude at said frequency $\omega 1$, output signal phase at said frequency $\omega 1$, linewidth, and relaxation time.

10. A method for performing magnetic resonance imaging on a selected portion of a sample, the method comprising:

providing a selected ferrimagnetic material into the sample by chemically bonding the ferrimagnetic material in particle format to the sample, the ferrimagnetic material having known ferromagnetic spin resonance characteristics, at least one resonant frequency $\omega=\omega 0$, and a diameter no greater than 1 $\mu$m, the ferrimagnetic material now a constituent of a selected portion of the sample;

applying an excitation electromagnetic field to the sample using an electromagnetic wave generator, the excitation electromagnetic field having at least one of a static component and a time varying component with a frequency $\omega=\omega 1 \approx \omega 0$, a selected magnetic field strength, and a selected magnetic field direction relative to the sample portion;

applying an external gradient magnetic field to the sample, the external gradient magnetic field having at least one of a static comnonent and a time varying component, a selected magnetic field direction, and at least first and second selected magnetic field strengths at at least first and second selected locations, respectively, within the sample portion, measuring at or near the resonant frequency $\omega 0$ of the ferrimagnetic material at least one of (i) a real component $\mu'(\omega 1)$ of the complex permeability parameter, and (ii) an imaginary component $\mu''(\omega 1)$ of the complex permeability parameter of the sample portion at each of the selected locations to determine at least one value of a material parameter at each of the selected locations; and constructing an image of the sample portion, by comparing the measured parameter values with corresponding reference values for the selected ferrimagnetic constituent for each of the selected locations;

the method further comprising choosing said frequency $\omega 1$ to be no greater than 1 GHz.

11. A method for performing magnetic resonance imaging on a selected portion of a sample, the method comprising:

providing a selected ferrimagnetic material into the sample by chemically bonding the ferrimagnetic material in particle format to the sample, the ferrimagnetic material having known ferromagnetic spin resonance characteristics and at least one resonant frequency $\omega=\omega 0$, wherein the ferrimagnetic material is now a constituent of a selected portion of the sample;

applying an excitation electromagnetic field to the sample using an electromagnetic wave generator, the excitation electromagnetic field having at least one of a static component and a time varying component with a frequency $\omega=\omega 1 \approx \omega 0$, a selected magnetic field strength, and a selected magnetic field direction relative to the sample portion;

applying an external gradient magnetic field to the sample, the external gradient magnetic field having at least one of a static component and a time varying component, a selected magnetic field direction, and at least first and second selected magnetic field strengths at at least first and second selected locations, respectively, within the sample portion;

measuring at or near the resonant frequency $\omega 0$ of the ferrimagnetic material at least one of (i) a real component $\mu'(\omega 1)$ of the complex permeability parameter, and (ii) an imaginary component $\mu''(\omega 1)$ of the complex permeability parameter of the sample portion at each of the selected locations to determine at least one value of a material parameter at each of the selected locations; and constructing an image of the sample portion, by comparing the measured parameter values with corresponding reference values for the selected ferrimagnetic constituent for each of the selected locations.

12. The method of claim 1, further comprising:

comparing at least one of said measured parameter values for each of said selected locations with said corresponding reference value for said selected ferrimagnetic constituent; and when said measured value and said corresponding reference value substantially agree, interpreting this condition as indicating that said selected ferrimagnetic constituent is associated with the sample portion at said selected location at which said material parameter measurement is taken.

13. The method of claim 11, further comprising:

when said measured value and said corresponding reference value do not substantially agree, interpreting this condition as indicating that said selected ferrimagnetic constituent is not associated with said sample portion at said selected location at which said material parameter measurement is taken.

14. The method of claim 11, further comprising the step of choosing the selected ferrimagnetic constituent from a group of ferrimagnetic compounds consisting of a compound $\{c\}_3(a)_2[d]_3O_{12}$, where $\{c\}$ is in dodecahedral form, (a) is in octahedral form, [d] is in tetrahedral form and the element c is drawn from a group consisting of $Na^{1+}$, $K^{1+}$, $Rb^{1+}$, $Tl^{1+}$, $Ag^{1+}$, $Au^{1+}$, $Hg^{1+}$, $Eu^{2+}$, $Ca^{2+}$, $Sr^{2+}$, $Ba^{2+}$, $Hg^{2+}$, $Pb^{2+}$, $Y^{3+}$, $La^{3+}$, $Gd^{3+}$, $Bi^{3+}$, $In^{3+}$, and $Sc^{3+}$.

15. The method of claim 11, further comprising the step of choosing the selected ferrimagnetic constituent from a group of ferrimagnetic compounds consisting of a compound $\{c\}_3(a)_2[d]_3O$, where $\{c\}$ is in dodecahedral form, (a) is in octrahedral form, [d] is in tetrahedral form and the element a is drawn from a group consisting of $Cu^{1+}$, $Mn^{2+}$, $Ni^{2+}$, $Zn^{2+}$, $Mg^{2+}$, $Fe^{3+}$, $Ru^{3+}$, $Cu^{3+}$, $Cr^{4+}$, $Mo^{4+}$, $W^{4+}$, $Al^{3+}$, $Ga^{3+}$, $In^{3+}$, $Sc^{3+}$, $Ti^{4+}$, $Zr^{4+}$, $Hf^{4+}$, $Si^{4+}$, $Ge^{4+}$, $Sn^{4+}$, $V^{5+}$, $Nb^{5+}$, $Ta^{5+}$, $P^{5+}$, $As^{5+}$, and $Sb^{5+}$.

16. The method of claim 11, further comprising the step of choosing the selected ferrimagnetic constituent from a group of ferrimagnetic compounds consisting of a compound $\{c\}_3(a)_2[d]_3O_{12}$, where $\{c\}$ is in dodecahedral form, (a) is in octahedral form, [d] is in tetrahedral form and the element d is drawn from a group consisting of $Cu^{1+}$, $Mn^{2+}$, $Ni^{2+}$, $Zn^{2+}$, $Mg^{2+}$, $Fe^{3+}$, $Ru^{3+}$, $V^{3+}$, $Nb^{3+}$, $Al^{3+}$, $Ga^{3+}$, $In^{3+}$, $Sc^{3+}$, $Cr^{4+}$, $Mo^{4+}$, $W^{4+}$, $Ti^{4+}$, $Zr^{4+}$, $Hf^{4+}$, $Si^{4+}$, $Ge^{4+}$, $Sn^{4+}$, $V^{5+}$, $Nb^{5+}$, $Ta^{5+}$, $P^{5+}$, $As^{5+}$, and $Sb^{5+}$.

17. The method of claim 11, further comprising the step of choosing the selected ferrimagnetic constituent from a group of ferrimagnetic compounds consisting of a compound $A[B]_2O_4$, where A is in tetrahedral form, B is in octahedral form, and the element A is drawn from a group consisting of $Cu^{1+}$, $Mn^{2+}$, $Ni^{2+}$, $Mg^{2+}$, $Zn^{2+}$, $Fe^{3+}$, $Ru^{3+}$, $V^{3+}$, $Nb^{3+}$, $Al^{3+}$, $Ga^{3+}$, $In^{3+}$, $Sc^{3+}$, $Cr^{4+}$, $Mo^{4+}$, $W^{4+}$, $Ti^{4+}$, $Zr^{4+}$, $Hf^{4+}$, $Si^{4+}$, $Ge^{4+}$, $Sn^{4+}$, $V^{5+}$, $Nb^{5+}$, $Ta^{5+}$, $P^{5+}$, $As^{5+}$, and $Sb^{5+}$.

18. The method of claim 1, further comprising the step of choosing the selected ferrimagnetic constituent from a group of ferrimagnetic compounds consisting of a compound $A[B]_2O_4$, where A is in tetrahedral form, B is in octahedral form, and the element B is drawn from a group consisting of $Cu^{1+}$, $Mn^{2+}$, $Ni^{2+}$, $Mg^{2+}$, $Zn^{2+}$, $Fe^{3+}$, $Ru^{3+}$, $V^{3+}$, $Nb^{3+}$, $Al^{3+}$, $Ga^{3+}$, $In^{3+}$, $Sc^{3+}$, $Cr^{4+}$, $Mo^{4+}$, $W^{4+}$, $Ti^{4+}$, $Zr^{4+}$, $Hf^{4+}$, $Si^{4+}$, $Ge^{4+}$, $Sn^{4+}$, $V^{5+}$, $Nb^{5+}$, $Ta^{5+}$, $P^{5+}$, $As^{5+}$, and $Sb^{5+}$.

19. The method of claim 11, further comprising choosing said measured material parameter value from the following group of parameter values: said at least one location of said ferrimagnetic constituent, output signal amplitude at said frequency $\omega 1$, output signal phase at said frequency $\omega 1$, linewidth, and relaxation time.

20. The method of claim 11, further comprising the step of choosing said frequency $\omega 1$ to be no greater than 1 GHz.

* * * * *